United States Patent [19]

Bartels-Keith et al.

[11] Patent Number: 4,526,965

[45] Date of Patent: Jul. 2, 1985

[54] URACIL DERIVATIVES OF THIO- AND SELENOUREA COMPOUNDS

[75] Inventors: James R. Bartels-Keith, Lexington; Anthony J. Puttick, Arlington, both of Mass.

[73] Assignee: Polaroid Corporation, Cambridge, Mass.

[21] Appl. No.: 533,265

[22] Filed: Sep. 16, 1983

[51] Int. Cl.$^3$ .................... C07D 239/54; G03C 1/10
[52] U.S. Cl. .................................. 544/311; 544/296; 260/550; 430/219; 430/240; 430/445
[58] Field of Search .......................................... 544/311

[56] References Cited

U.S. PATENT DOCUMENTS 3,920,653 11/1975 Wenzelburger et al. ........... 544/311
4,442,290 4/1984 Bartels-Keith et al. ............ 544/310

OTHER PUBLICATIONS

Hoppe-Seyler's Z. Physiol. Chem., Cytostatische Thymin Derivate des Imidazolthions-(2), Guglielmi, 349 (12), pp. 1733-1738, (1968).
Hoppe-Seyler's Z. Physiol. Chem., Tumor Inhibitors. IV. Cytostatic and Thyrostatic Effects of Thioethers of 2-Mercaptoimidazole, Weitzel et al, (10), pp. 1277-1284, (1967).
Hoppe-Seyler's Z. Physiol. Chem., Ribofuranosides of Cytostatic Thymine Derivatives of Imidazole-2-Thione, Guglielmi et al, 350 (6), pp. 710-716, (1969).
Hoppe-Seyler's Z. Physiol. Chem., Metabolic Properties of Tumor Slices Under Influence of Cytostatic Compounds, Athen et al, 350 (7), pp. 803-808, (1969).
Hoppe-Seyler's Z. Physiol Chem., α and β Thymidine Thioethers of 2-Imidazolethione, Guglielmi et al, 350 (7), pp. 809-814, (1969).
Hoppe-Seyler's Z. Physiol. Chem., Cytostatic Effects of Thymine Thioethers of Imidazole-2-Thione, Guglielmi et al, 350 (11), pp. 1394-1400, (1969).

*Primary Examiner*—Donald G. Daus
*Assistant Examiner*—Cecilia Shen
*Attorney, Agent, or Firm*—Gaetano D. Maccarone

[57] ABSTRACT

Novel compounds which release thio- or selenourea moieties or derivatives thereof upon contact with aqueous alkaline compositions and are therefore useful in photographic applications. The compounds include, in addition to the thio- or selenourea moiety, a uracil blocking moiety and an anion.

6 Claims, No Drawings

URACIL DERIVATIVES OF THIO- AND SELENOUREA COMPOUNDS

BACKGROUND OF THE INVENTION

In various photographic systems for forming images, whether in black or white or in color, it is often desirable to include in the photographic film unit one or more of the various photographic reagents required for development and/or to enhance image quality. This practice extends both to conventional systems for forming negative images and also to various systems such as diffusion transfer wherein a positive image in silver or in color is obtained.

In many instances, the photographic reagent may be contained initially in either the processing composition applied for development and image formation or in the film unit itself. The latter is typically preferred so as to reduce the number of ingredients required in the processing composition.

In other instances, the particular photographic reagent desired is not sufficiently stable in alkali to provide the requisite shelf life for the processing composition or the reagent is incompatible and/or reacts with another reagent in the processing composition and therefore must be contained initially in the film unit.

In still other instances, the reagent must be provided at some particular time in the development process which requires that it be present in a specified layer or in specified proximity to another layer in the film unit.

In all of the foregoing instances, it is desirable that the reagent be contained in the desired layer(s) of the film unit in a form which is stable and non-migratory or non-diffusible and yet available when it is required at a particular time in the development process. To accomplish this result, it is known in the art to attach to the particular photographic reagent a blocking moiety which prevents the photographic reagent from reacting with other photographic materials present in the film unit or migrating or diffusing prior to the time when photographic development is effected but which will release the photographic reagent at the desired time such as by reaction with the aqueous alkaline processing composition.

The present application relates to novel compounds which release a thio- or selenourea moiety or derivatives thereof upon contact with aqueous alkaline compositions and which are useful in photographic applications.

SUMMARY OF THE INVENTION

It is therefore an object of the invention to provide novel compounds.

It is another object of the invention to provide compounds which are useful in photographic applications.

A further object is to provide compounds which provide controlled release of a thio- or selenourea moiety or a derivative thereof during development of an exposed photosensitive element.

BRIEF SUMMARY OF THE INVENTION

These and other objects and advantages are accomplished in accordance with the invention by providing novel compounds which are represented by the formula

FORMULA A

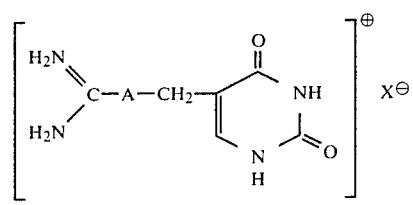

wherein A is sulfur or selenium and X is an anion such as chloride, a naphthalene sulfonate such as 2-naphthalene sulfonate, tetraphenyl borate and the like.

It should be noted that some of the compounds within Formula A may be isolated as hydrates depending upon the preparative procedures employed and such compounds are intended to be encompassed by Formula A.

It should also be noted that both the uracil and the thio- or selenourea moieties may be substituted in any of the available positions. Thus, compounds within Formula A may be represented by the formula

FORMULA B

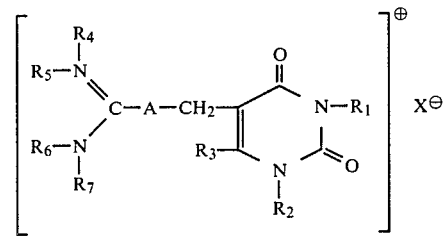

wherein $R_1$ is H, alkyl or a group which is hydrolyzable upon contact with an aqueous alkaline composition; $R_2$ is H or a hydrolyzable group; $R_3$ is H or alkyl having from 1 to 6 carbon atoms; $R_4$, $R_5$, $R_6$ and $R_7$ can be the same or different and can be hydrogen, alkyl, preferably having from 1 to 6 carbon atoms, aryl such as phenyl, acyl such as acetyl or benzoyl, amino, amino substituted with alkyl having from 1 to 6 carbon atoms, or two or more of these substituents, taken together with the nitrogen atoms, can form part of a heterocyclic ring structure including substituted rings and fused or condensed rings; and A and X are as previously defined.

It is preferred to have at least one and optimally two or more of $R_4$, $R_5$, $R_6$ and $R_7$ as alkyl having from 1 to 6 carbon atoms. Experiments have shown that the presence of such substituents typically minimizes alternative competing cleavage reactions which could result in the formation of by-products in addition to the desired photographic reagent. In the case where $R_4$, $R_5$, $R_6$ and $R_7$ are hydrogen, for maximum rate of release it is preferred to have $R_1$ and $R_2$ as hydrogen and $R_3$ as hydrogen or alkyl having from 1 to 6 carbon atoms.

Typical suitable hydrolyzable groups which are useful as substituents for $R_1$ and $R_2$ include, for example, acyl groups such acetyl or benzoyl; ester groups such as

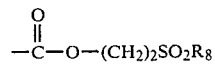

where $R_8$ is alkyl, preferably having from 1 to 6 carbon atoms, or aryl such as phenyl, or

and —$CH_2$—$CH_2$—Y where Y is

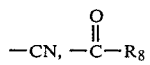

or $SO_2$—$R_8$.

The compounds cleave in alkaline composition to provide a controlled release of the thio- or selenourea moiety or derivative thereof which are useful as toning agents and silver halide solvents. The rate of release of the photographic reagent is typically dependent upon the hydroxyl ion concentration of the alkaline medium, temperature and also upon electrostatic effects brought about by the ionization of atoms in the molecule upon contact with the aqueous alkaline medium which could reduce the rate at which the release mechanism occurs. Such variables permit the selection of a compound having release rates desired for a particular application.

DESCRIPTION OF THE PREFERRED EMBODIMENTS

Preferred compounds according to the invention are represented by the formulas

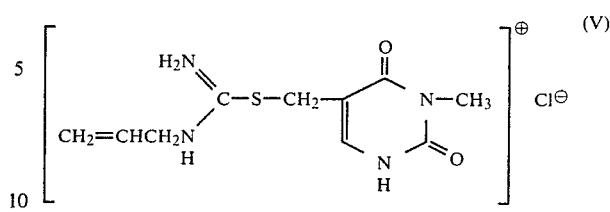

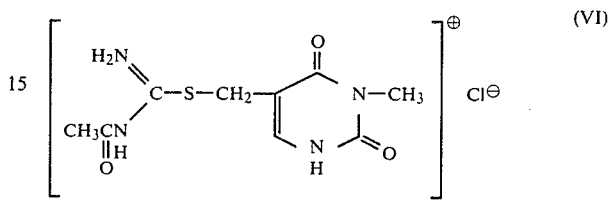

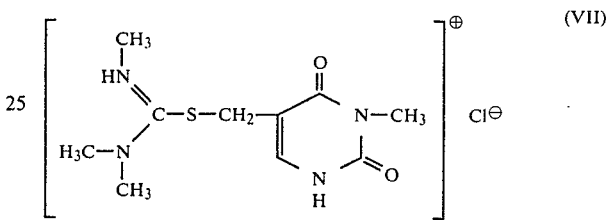

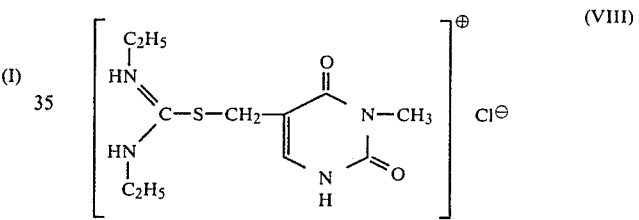

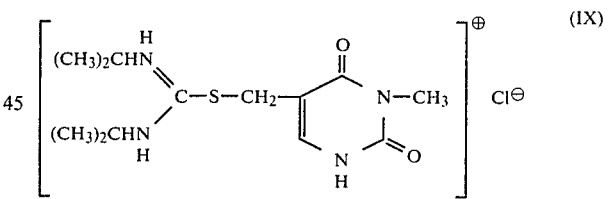

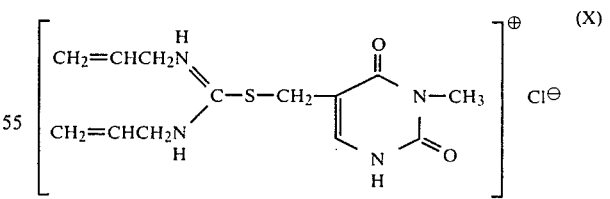

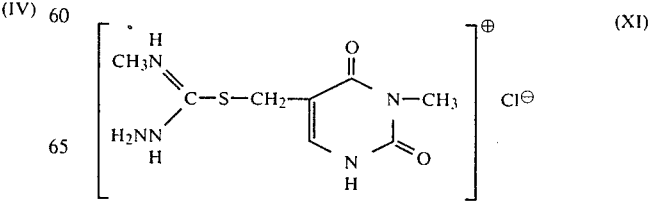

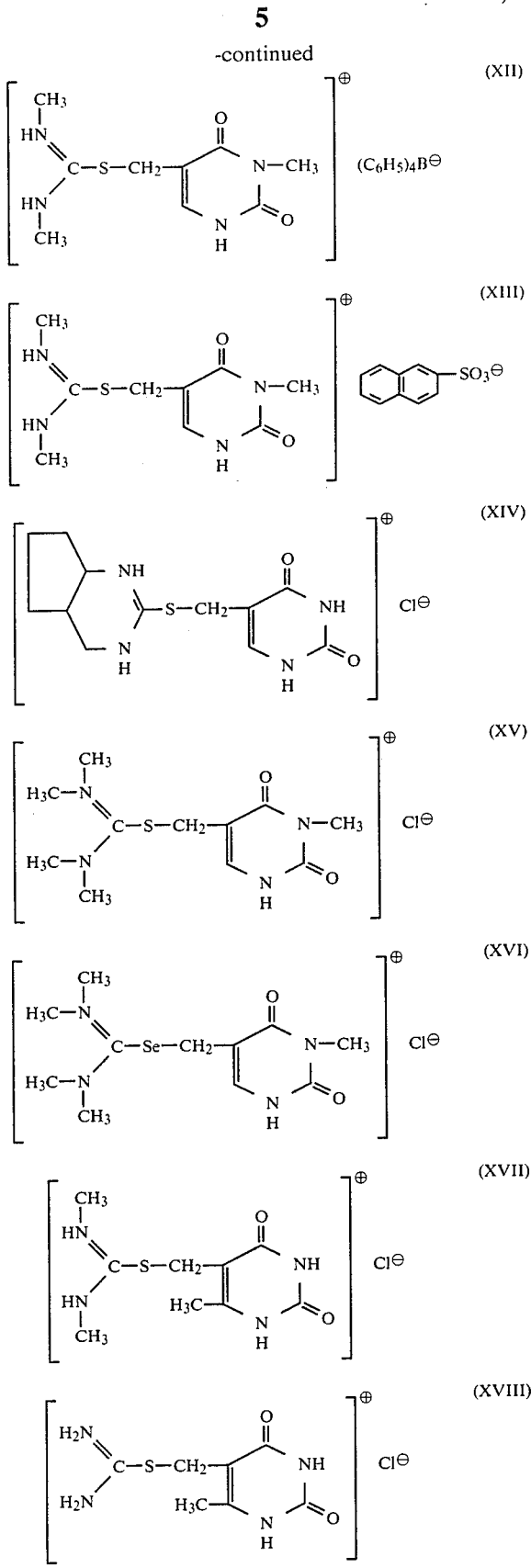

The compounds of the invention may be prepared according to reactions which are well known in the art and such techniques will be apparent from the specific examples provided herein. Generally, the compounds can be prepared by reacting thio- or selenourea or a suitably substituted derivative thereof with 5-chloromethyl uracil or a substituted derivative thereof in a solvent such as dimethylformamide.

As mentioned previously, the thio- or selenourea moieties which are released when the compounds of the invention come in contact with aqueous alkaline compositions are useful in photographic applications as toning agents and silver halide solvents among others. Thus, the compounds of the invention are useful in any photographic system wherein controlled release of a toning agent or a silver halide solvent is desired.

The invention will now be described further in detail by way of examples, it being understood that these are intented to be illustrative only and the invention is not intended to be limited to the materials, conditions, process parameters, etc. which are recited therein. All parts and percentages are by weight unless otherwise indicated.

EXAMPLE I

Thiourea (0.76 g, 0.01 m) and 5-chloromethyl-3-methyluracil (1.75 g, 0.01 m) were stirred at 60° C. under nitrogen for 15 minutes in 10 ml of dimethylformamide. The resulting colorless solution was cooled and poured into 100 ml of diethyl ether slowly with stirring. The resulting colorless gummy precipitate crystallized upon cooling in an ice/salt bath with scratching. The solid was collected by filtration, washed with diethyl ether and dried in air to give 2.37 g (94% yield) of Compound III, a colorless powder, m.p. 216°–8° C. (dec.)

$C_7H_{11}N_4O_2SCl$ requires 33.53%C, 4.39%H, 22.36%N, 12.77%O, 12.77%S and 14.17%Cl. Elemental analysis found 34.16%C, 4.91%H, 21.99%N, 12.72%O, 12.55%S and 13.73%Cl.

The structure of the compound was confirmed by IR, $^{13}$C NMR and mass spectra.

EXAMPLE II

A mixture of N,N'-dimethylthiourea (1.04 g, 0.01 m) and 5-chloromethyl-3-methyluracil (1.75 g, 0.01 m) in 25 ml of dimethylformamide was stirred at 60° C. under nitrogen for 15 minutes during which time a partial solution formed followed by precipitation of a solid. The mixture was cooled and diluted with 100 ml of diethyl ether. The resulting sticky precipitate crystallized upon scratching at 0° C. for 10 minutes. The solid was collected, washed with diethyl ether and air dried to give 2.71 g (97% yield) of Compound IV, a colorless powder, m.p. 203°–4° C. (dec.)

$C_9H_{15}N_4O_2SCl$ requires 38.78%C, 5.39%H, 20.11%N, 11.50%O, 11.50%S and 12.75%Cl. Elemental analysis found 38.93%C, 5.47%H, 20.12%N, 11.44%O, 11.51%S and 12.66%Cl.

The structure of the compound was confirmed by IR, $^{13}$C NMR and mass spectra.

EXAMPLE III

A mixture of 5-chloromethyl-3-methyluracil (1.75 g, 0.10 m) and 1-allyl-2-thiourea (1.16 g, 0.10 m) in 15 ml of dimethylformamide was stirred under nitrogen at 60° C. for 15 minutes. The resulting colorless solution was cooled and diluted with 100 ml of diethyl ether. The ether was decanted and replaced with acetone. Upon standing overnight a solid crystallized out of solution. The solid was collected by filtration, washed with acetone and dried in air to give 2.66 g (92% yield) of Compound V, a colorless solid, m.p. 192°–4° C. (dec.).

$C_{10}H_{15}N_4O_2SCl$ requires 41.31%C, 5.16%H, 19.28%N, 11.02%O, 11.02% and 12.22%Cl. Elemental analysis found 41.43%C, 5.32%H, 19.05%N, 11.22%O, 11.00%S and 12.05%Cl.

The structure of the compound was confirmed by IR, $^{13}C$ NMR and mass spectra.

EXAMPLE IV

A solution of Compound IV (1.39 g, 0.005 m) in 25 ml of water and a solution of sodium tetraphenylborate (1.71 g, 0.005 m) were stirred together. The resulting thick colorless precipitate was collected, washed well with water and dried in air to give 2.68 g (94% yield) of Compound XII, a colorless powder, m.p. 102°–4° C. (dec 134° C.).

$C_9H_{15}N_4O_2S\cdot C_{24}H_{20}B$ 0.1/2$H_2O$ requires 69.35%C, 6.35%H, 9.80%N and 5.61%S. Elemental analysis found 69.11%C, 6.32%H, 9.70%N and 5.63%S.

The structure of the compound was confirmed by IR and $^{13}C$ NMR spectra.

EXAMPLE V

A solution of 2-naphthalene sulfonic acid sodium salt (2.30 g, 0.01 m) in 20 ml of water was mixed with a solution of Compound IV (2.78 g, 0.10 m) in 10 ml of water and the resulting clear solution chilled in an ice bath and scratched with a glass rod. This was stored in a refrigerator overnight and the solid which separated was collected, washed sparingly with water and dried in air to give 3.28 g (67% yield) of Compound XIII, a colorless powder, m.p. 73°–74° C.

$C_9H_{15}N_4O_2S\cdot C_{10}H_7O_3S\cdot 2H_2O$ requires 46.90%C, 5.39%H, 11.51%N, 23.02%O and 13.18%S. Elemental analysis found 46.74%C, 5.36%H, 11.52%N, 22.93%O and 13.25%S.

The structure of the compound was confirmed by IR and $^{13}C$ NMR spectra.

EXAMPLE VI

To a solution of 4-methylthiosemicarbazide (2.10 g, 0.02 m) in 25 ml of dimethylformamide at 80° C. there was added 3.49 g (0.02 m) of 5-chloromethyl-3-methyluracil and the resulting pale yellow solution was stirred for 10 minutes. The resulting precipitate was collected from the cooled solution, washed with dimethylformamide and then with diethyl ether and dried in air to give 4.15 g (74% yield) of Compound XI, a colorless powder, m.p. 172°–4° C. (dec).

$C_8H_{14}N_5O_2SCl$ requires 34.35%C, 5.04%H, 25.03%N, 11.44%O, 11.46%S and 12.67%Cl. Elemental analysis found 34.47%C, 5.03%H, 24.88%N, 11.56%O, 11.44%S and 12.54%Cl.

The structure of the compound was confirmed by IR and $^{13}C$ NMR spectra.

EXAMPLE VII

A mixture of hexahydro-4,5-trimethylenepyrimidine-2-thione (1.56 g) and 5-chloromethyluracil (1.6 g) in 80 ml of acetone was refluxed under nitrogen for 18 hours. The solution was cooled and the solid collected by filtration. The solid was then stirred in boiling acetone and again collected by filtration to give 2.2 g of Compound XIV.

The structure of the product was confirmed by $^{13}C$ NMR and IR spectra.

$C_{12}H_{17}N_4O_2S\cdot Cl$ requires 45.49%C, 5.41%H, 17.69%N 10.13%S and 11.20%Cl. Elemental analysis found 45.37%C, 5.59%H, 17.71%N, 9.91%S and 11.18%Cl.

EXAMPLE VIII

A solution of tetramethylselenourea (537.4 mg, 3.00 mmol) in 1 ml of dimethylformamide was filtered through a diatomaceous earth pad and the pad was washed with four 0.5 ml portions of dimethylformamide. The combined filtrates were added to a solution of 5-chloromethyl-3-methyluracil (523.8 mg, 3.00 mmol) in 3 ml of dimethylformamide to give a clear solution from which a white crystalline precipitate separated upon standing for a few minutes. The misture was stirred under nitrogen in the dark for 23 hours. The resulting slightly pinkish solid was collected, washed successively with dry dimethylformamide, ether, benzene and ether, transferred quickly to a dessicator and dried under vacuum for 16 hours to give 1146 mg (87% yield) of compound XVI, m.p. 169°–170° C.

The structure of the product was confirmed by $^{13}C$ NMR, IR and mass spectra.

$C_{14}H_{27.5}N_5O_{3.75}SeCl$ requires 38.19%C, 6.30%H, 15.91%N, 13.63%O, 17.93%Se and 8.05%Cl. Elemental analysis found 38.49%C, 6.26%H, 16.05%N, 13.68%O, 17.73%Se and 7.95%Cl.

EXAMPLE IX

To a solution of N,N'-dimethylthiourea (2.08 g, 0.020 m) in 25 ml of dimethylformamide there was added 5-chloromethyl-6-methyluracil (3.50 g, 0.020 m) and the resulting solution stirred under dry nitrogen at 75° C. for 10 minutes. The resulting colorless precipitate was collected by filtration, washed with acetone and dried in air to give 5.33 g (96% yield) of Compound XVII, a colorless powder, m.p. 226°–227° C. (dec.).

The structure of the product was confirmed by $^{13}C$ NMR and IR spectra.

$C_9H_{15}N_4O_2SCl$ requires 38.78%C, 5.42%H, 20.10%N, 11.48%O, 11.50%S and 12.72%Cl. Elemental analysis found 38.90%C, 5.40%H, 20.08%N, 11.52%S and 12.68%Cl.

EXAMPLE X

To a solution of thiourea (1.52 g, 0.020 m) in 25 ml of dimethylformamide there was added 5-chloromethyl-6-methyluracil (3.50 g, 0.020 m) and the resulting solution stirred under dry nitrogen at 75° C. for 10 minutes. A colorless precipitate formed. The mixture was cooled to room temperature and the precipitate was collected by filtration, washed with acetone and dried in air to give 4.77 g (95% yield) of Compound XVIII, a colorless powder, m.p. 241°–242° C. (dec.).

The structure of the product was confirmed by IR and $^{13}C$ NMR spectra.

$C_7H_{11}N_4O_2SCl$ requires 33.54%C, 4.42%H, 22.35%N, 12.76%O, 12.79%S and 14.14%Cl. Elemental analysis found 33.71%C, 4.59%H, 22.23%N, 12.76%O, 12.63%S and 14.13%Cl.

Althouth the invention has been described with respect to various preferred embodiments it is not intended to be limited thereto but rather those skilled in the art will recognize that variations and modifications may be made therein which are within the spirit of the invention and the scope of the appended claims.

What is claimed is:

1. A compound represented by the formula

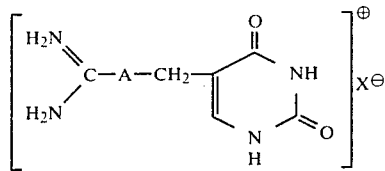

where A is sulfur or selenium and X is an anion.

2. A compound as defined in claim 1 wherein A is sulfur.

3. A compound as defined in claim 1 which is represented by the formula

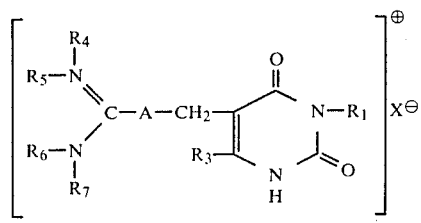

wherein $R_1$ is hydrogen or alkyl having from 1 to 6 carbon atoms; $R_3$ is hydrogen or alkyl having from 1 to 6 carbon atoms; and $R_4$, $R_5$, $R_6$ and $R_7$ are the same or different and are hydrogen, alkyl, phenyl, acetyl, benzoyl, amino or amino substituted with alkyl having from 1 to 6 carbon atoms.

4. A compound as defined in claim 3 wherein A is sulfur.

5. A compound as defined in claim 3 wherein at least one of $R_4$, $R_5$, $R_6$ and $R_7$ is alkyl having from 1 to 6 carbon atoms.

6. A compound as defined in claim 3 wherein $R_1$ is hydrogen, $R_3$ is hydrogen or alkyl having from 1 to 6 carbon atoms and $R_4$, $R_5$, $R_6$ are each hydrogen.

* * * * *